United States Patent [19]

Langdon

[11] Patent Number: 4,510,306

[45] Date of Patent: Apr. 9, 1985

[54] METHOD FOR PURIFYING REACTION PRODUCTS CONTAINING HIGHER-ALKYL GLYCOSIDES

[75] Inventor: William K. Langdon, Grosse Ile, Mich.

[73] Assignee: BASF Wyandotte Corporation, Wyandotte, Mich.

[21] Appl. No.: 531,927

[22] Filed: Sep. 13, 1983

Related U.S. Application Data

[63] Continuation-in-part of Ser. No. 327,341, Dec. 4, 1981, abandoned.

[51] Int. Cl.³ .................. C07H 1/06; C07H 15/04
[52] U.S. Cl. .................. 536/127; 536/124; 536/18.6
[58] Field of Search .................. 536/4.1, 127, 18.6

[56] References Cited

U.S. PATENT DOCUMENTS 2,559,519 7/1951 Smith .................. 203/50
3,580,850 5/1971 Dupre .................. 252/186.1
3,598,865 8/1971 Lew .................. 252/174.17
3,772,269 11/1973 Lew .................. 8/611
4,349,669 9/1982 Klahr .................. 536/127

FOREIGN PATENT DOCUMENTS 3001064 7/1981 Fed. Rep. of Germany .

Primary Examiner—Donald B. Moyer
Assistant Examiner—C. Joseph Faraci
Attorney, Agent, or Firm—Joseph D. Michaels

[57] ABSTRACT

The subject invention relates to the removal of residual higher alcohols which are present from the preparation of crude higher-alkyl glycosides. The residual higher alcohols are removed via vacuum distillation with a hydroxyl-containing solvent. The purified higher-alkyl glycosides are biodegradable nonionic surfactants which are soluble and stable in highly alkaline cleaning formulations used for bottle washing, metal cleaning, textile treatment and other applications.

2 Claims, No Drawings

METHOD FOR PURIFYING REACTION PRODUCTS CONTAINING HIGHER-ALKYL GLYCOSIDES

This application is a continuation-in-part of copending application, now abandoned, filed on Dec. 4, 1981, as Ser. No. 327,341.

BACKGROUND OF THE INVENTION

1. Field of the Invention

The subject invention relates to the purification of crude higher-alkyl glycosides by removal of residual higher boiling aliphatic monohydroxyl compounds which are used in the preparation of the crude higher-alkyl glycosides. The residual higher alcohols are removed via distillation using an added high boiling hydroxyl-containing solvent to assist in the separation. The product can then be further treated to improve color.

2. Description of the Prior Art

It is known that crude higher-alkyl glycosides can be prepared by reacting a monosaccharide or a compound hydrolyzable to a monosaccharide with a monohydric alcohol having from 8 to 25 carbon atoms. See for example U.S. Pat. Nos. 3,598,865 and 3,772,269. These methods result in undesirable amounts of odorous higher alcohols, which are used as reactants in the synthesis, remaining in the crude higher-alkyl glycoside. The presence of these alcoholic impurities results in the products being unsuitable for many applications, particularly those that are involved in contact with human beings or with equipment used in food processing.

SUMMARY OF THE INVENTION

A method for purifying crude higher-alkyl glycosides has been discovered which comprises partially distilling the crude higher-alkyl glycoside in mixture with a hydroxyl-containing solvent selected from the group consisting of glycerol, polyoxyalkylene glycols having an average of 3 to 5 oxyalkylene units selected from the group consisting of oxyethylene and oxypropylene, $C_1$–$C_4$ alkyl ethers of polyoxyalkylene glycols having from 2 to about 5 oxyalkylene units selected from the group consisting of oxyethylene and oxypropylene, and $C_1$–$C_4$ alkyl ethers of aliphatic diols, triols and tetrols having no more than 4 carbon atoms.

The purified higher-alkyl glycosides are biodegradable nonionic surfactants which are soluble and stable in highly alkaline cleaning formulations used for bottle washing, metal cleaning, textile treating, and other applications. They are free of odorous higher alcohols normally found in higher-alkyl glycoside products. The removal of the alcoholic impurities results in their being especially useful in applications involving contact with human beings or with equipment used in food processing.

DESCRIPTION OF THE PREFERRED EMBODIMENT

The crude higher-alkyl glycosides which are to be purified in accordance with process of the subject invention can be prepared by any of several methods known in the art. One such process found to be suitable is that of U.S. Pat. No. 3,772,269 which is incorporated herein by reference. In the present work, corn starch was used as a saccharide source; sulfuric acid, as the catalyst; and propylene glycol, as a solvent-coreactant for reaction with various higher molecular weight alcohols. For details of the process, see the referenced patent.

Whether prepared by the above process or some modification thereof (as, for example, using a $C_1$–$C_4$ alcohol instead of propylene glycol), the crude higher-alkyl glycoside is normally contaminated with residual higher alcohol. Even though these products are stripped to final temperature and pressure conditions which exceed the boiling point of the higher alcohol, the latter is held tenaciously by the crude glycoside. This residual free higher alcohol confers an obnoxious odor to the crude glycoside and reduces its utility.

The crude glycoside is a complex mixture of compounds wherein the amounts and nature of the components depend on the raw materials and process used for manufacture. The predominant component is, of course, the higher-alkyl glycoside although, depending on the mole ratio of higher alcohol to anhydroglucose units (AHG) used, some of the glycoside could have two or more saccharide units per acetal group. Also present are glycosides from propylene glycol (mono- and diglycosides) or from lower alcohol (if used). Except for the residual higher alcohol, none of these components interferes with the behavior and properties of the higher-alkyl glycoside in normal uses.

In accordance with the present invention, residual higher alcohol present in the crude higher-alkyl glycoside is removed by distillation with the assistance of an added hydroxyl-containing solvent. While not wanting to be bound by theory, it appears that, mechanically, the solvent serves a twofold purpose in the distillation. It maintains a fluid product, thereby enhancing the lability of the free higher alcohol and it codistills with the free higher alcohol thereby "sweeping" the undesired alcohol from the product. Chemically, the solvent can serve to release the higher alcohol from a complex (e.g., hydrogen bonded) with the glycoside. The solvent is selected as indicated hereinafter.

To carry out the process of this invention, the solvent is charged, along with the crude higher-alkyl glycoside which is to be purified, to a flask fitted with a mechanical stirrer, a thermometer, a distillation head, and equipped for heating and for operation at reduced pressure. The mixture is stirred and heated while the pressure is slowly reduced. Distillate, consisting of solvent and higher alcohol, is collected over a period of several hours until the final condition of a pressure of 3 to 5 torr and a pot temperature of 150° to 175° C. depending on the higher alcohol being removed. The stripping is completed when the rate of distillation at the final condition indicated declines rapidly to essentially zero.

The high boiling hydroxyl-containing solvent used to purify the crude higher-alkyl glycoside is selected from the group consisting of glycerol, polyoxyalkylene glycols having an average of 3 to about 5 oxyalkylene units selected from the group consisting of oxyethylene and oxypropylene, $C_1$–$C_4$ alkyl ethers of polyoxyalkylene glycols having an average of 2 to about 5 oxyalkylene units selected from the group consisting of oxyethylene and oxypropylene, and $C_1$–$C_4$ alkyl ethers of aliphatic diols, triols, and tetrols having no more than 4 carbon atoms. Examples of such solvents are glycerol, tripropylene glycol, triethylene glycol, tetraethylene glycol, pentapropylene glycol, monobutyl ether of glycerol, diethyl ether of erythritol, methyl ether of pentaethylene glycol. Glycerol and the polyoxyalkylene glycols are preferred.

The essential feature of the solvent, which is heated with alkyl glycoside, is that it is soluble in and compatible with the higher-alkyl glycoside, and has a boiling point equal to or greater than that of the higher alcohol used to form the higher-alkyl glycoside. It should also have a sufficiently high vapor pressure to partially codistill with the alcohol and be sufficiently high boiling that a portion is retained in the alkyl glycoside product. Finally, it should be non-toxic, soluble, and chemically and physically compatible with the alkyl glycoside. Besides removal of the higher alcohol, certain advantages can be gained from the presence of the solvent in the end product. One of these advantages is that the higher-alkyl glycoside product has a reduced viscosity and there is a reduced tendency for it to crystallize from solution.

In order to function satisfactorily, the boiling point of the solvent should be at least 110° C. at 5 torr, and preferably at least 10° C. higher than that of the highest boiling alcohol used to prepare the crude higher-alkyl glycoside. Thus, if the glycoside is prepared from an alcohol that contains dodecyl alcohol, the boiling point should be equal to or greater than 130° C. at 5 torr, and if the alcohol contains cetyl alcohol, the boiling point should be equal to or greater than 170° C. at 5 torr. The solvent may boil substantially higher than the alcohol, provided the vacuum stripping temperature and pressure conditions result in partial distillation of the solvent. Thus, glycerol can be used as a distillation solvent for decyl alcohol which has a boiling point of about 95° C. at 5 torr, even though glycerol has a boiling point of 155° C. at this pressure.

The amount of solvent normally used is from 5 percent to about 20 percent by weight based on the crude higher-alkyl glycoside. More than 20 percent can be used, particularly if residual solvent is desired as a diluent to improve viscosity, stability to crystallization, or for beneficial use in an application formulation.

It has also been found that for some applications it is desirable to lighten the color of the purified higher-alkyl glycoside. This can be accomplished by treating the higher-alkyl glycoside with a decolorizing agent which liberates oxygen such as hydrogen peroxide, sodium perborate, benzoyl peroxide, sodium hypochlorite, dichlorodimethylhydantoin, sodium persulfate, potassium persulfate, and sodium dichloroisocyanurate. Only minor amounts of such compounds are needed such as from 0.1 to 1 percent by weight based upon the weight of the higher-alkyl glycoside.

The examples which follow will provide specific details related to the practice of this invention but are not intended to limit its scope. All parts referred to in the examples are by weight and all temperatures are in degrees Centigrade, unless otherwise designated.

The abbreviations which follow are used to designate ingredients used in the examples:

A-1012—a mixture of $C_{10}$ and $C_{12}$ alcohols sold by Conoco Chemicals under the tradename of ALFOL 1012.
A-1214—a mixture of $C_{12}$ and $C_{14}$ alcohols sold by Conoco Chemicals under the tradename of ALFOL 1214.
GLY—glycerol.
P-1—an ethylene oxide adduct of ethylene glycol having an average molecular weight of 200.
P-2—a propylene oxide adduct of propylene glycol having an average molecular weight of 242.

EXAMPLE 1

Preparation of Crude Alkyl Glucoside

A reaction product containing higher-alkyl glycosides was prepared for purification by adding 798 parts of propylene glycol and 644 parts of corn starch to a four-neck flask equipped with a stirrer, thermometer, addition funnel, a distillation head and a vacuum source. With an agitator running, 4.2 parts of sulfuric acid and 9.4 parts of 50 percent hypophosphorus acid were added. After warming to 103° C. at 185 torr, distillation of the water was started. (Starch contains about 12 percent of adsorbed water.) The mixture was heated for 3 hours at a temperature in the range of 102° C. to 116° C. as the pressure was reduced to 50 torr while 109 parts of water-glycol distillate was collected. The mixture became clear as a result of glycolysis of the starch to form propylene glycol glucoside. Several hours later, 2310 parts of A-1012 were added over a 1 hour period at 75° C. The mixture was then heated at 126° C. at 70 torr for approximately 2 hours. During this time, a small amount of solids, which had precipitated, dissolved. The distillate which contained approximately 65 percent propylene glycol and 35 percent higher alcohols, was collected at a temperature of 113° C. at a pressure gradually reduced from 70 torr to 16 torr. The amount of distillate collected was 578 parts. The mixture was cooled, and 9 parts of 50 percent sodium hydroxide solution were added to neutralize the catalyst. The amount of crude product was 3087 parts. The product was a mixture of propylene glycol, A-1012, propylene glycol glucoside, and A-1012 glucoside.

Purification

Into a 1-liter flask equipped as described above, 617 parts of the product of the above synthesis were added. The mixture was heated to 127° C. while the pressure was reduced to 30 torr. Propylene glycol and alcohol distillate amounting to 411 parts were collected over a 3.5 hour period while the pressure was reduced from 30 torr to 3 torr. At this stage, the product contained residual alcohol which resulted in a strong odor. While still under reduced pressure, 20 parts of glycerol were added, and volatiles, including part of the glycerol, were removed by distillation up to a pot temperature of 150° C. at a pressure of 3 torr. The amount of distillate was 11 parts. The product, which amounted to 210 parts, was diluted with water to provide a 75 percent aqueous solution. The higher-alkyl glucoside had no alcohol odor.

EXAMPLE 2

The purification step of Example 1 was repeated with a second aliquot except 20 parts of P-1 were used instead of glycerol. The volatiles were removed up to a temperature of 160° C. at less than 5 torr. The weight of distillate collected was 7 grams and the weight of product was 219.7 grams. The product had no alcohol odor.

EXAMPLE 3

Crude higher-alkyl glycoside was prepared as in Example 1 except the following ingredients were used: 912 parts of propylene glycol (12 moles), 552 parts of corn starch (3 AGU), 4.8 parts of sulfuric acid, 8.0 parts of hypophosphorus acid, 2412 parts of A-1214 alcohol ($C_{12}C_{14}$ blend manufactured by Conoco), and 8.5 parts of caustic soda. In order to purify the product after distilling at a temperature of 166° C. at a pressure of less than 5 torr, 100 grams of glycerol were added and the distillate was collected up to a temperature of 168° at less than 5 torr. The weight of alcohol and glycerol that codistilled was 127 grams. The weight of product was 936 grams. The product had no alcohol odor.

EXAMPLE 4

Crude higher-alkyl glycoside was prepared as in Example 1 except the following ingredients were used: 258 parts of starch, 426 parts of propylene glycol, 924 parts of A-1012, 2.2 parts of sulfuric acid, and 4.0 parts 50 percent sodium hydroxide. A water fraction amounting to 34 parts was collected while the mixture was heated to 104° C. at a pressure of 42 torr, and then a second fraction amounting to 35 parts, which contained chiefly propylene glycol, was collected up to a temperature of 115° C. and 33 torr. Obtained were 404 parts of distillate, rich in propylene glycol, at 110° C. while the pressure was reduced to 11 torr. Then, the caustic soda was added to neutralize the catalyst, and subsequently, an alcohol-rich fraction weighing 722 parts was collected while the temperature was raised to 161° C. with the pressure being gradually reduced to less than 5 torr. At this point, 60 parts of glycerol were added, and the mixture was stripped up to 170° C. at less than 5 torr during which 57 parts of distillate were collected. The distillate separated into a lower glycerol layer and an upper alcohol layer. The alcohol layer, which weighed 39.8 parts was saved for recycle to the next glycoside preparation. The residue amounting to 410 grams was diluted with 176 parts of water to provide a 70 percent aqueous solution. The product had no odor of alcohol.

EXAMPLE 5

Example 4 was duplicated except P-2 was used as the solvent. (A separate distillation test made on P-2 at less than 5 torr indicated that 71.5 weight percent is distillable over the range of 124° C. to 175° C.) After distilling up to a pot temperature of 160° C. at less than 5 torr, 60 grams of P-2 was added and stripping was completed up to a pot temperature of 175° C. at less than 5 torr. The weight of distillate was 37 parts. Upon dilution of this distillate with 2 parts of water, 17.4 parts of alcohol separated. The product was free of alcohol odor.

Table I which follows summarizes the properties of the purified crude higher-alkyl glycosides.

TABLE I*

| Example | pH | Cloud Point | Surface Tension (dynes/cm) | Draves Sink Time (sec) |
|---|---|---|---|---|
| 1 | 7.2 | >100° C. | 29.7 | 16 |
| 2 | 7.0 | >100° C. | 29.5 | 25 |
| 3 | 6.5 | — | 29.8 | 45 |
| 4 | 7.6 | >100° C. | 30 | 30 |
| 5 | 9.5 | >100° C. | 27.8 | 24.3 |

*The pH and cloud point were measured at a 1 percent concentration while the surface tension and sink time were measured at a 0.1 percent concentration.

Examples 6 to 11 which follow illustrate the use of decolorizing agents to lighten the color of the purified products. In these examples, the higher-alkyl glucoside prepared in accordance with Example 4 was utilized. Before treatment, the product had a Gardner color of 4 to 5 as determined on a 10 percent solution.

EXAMPLE 6

In a reaction vessel, 415 parts of the higher-alkyl glucoside of Example 4 was diluted with 178 parts of water to form a 70 percent solution. Twelve parts of 30 percent hydrogen peroxide were added gradually, with the temperature maintained at about 70° C. and the pH maintained at 7 to 8 by the addition of a small amount of 50 percent caustic soda solution. The color of a 10 percent solution as determined by the Gardner method was less than 1 and by the APHA method, less than 100.

EXAMPLE 7

In a reaction vessel, 0.2 part of benzoyl peroxide was added to 50 parts of the 70 percent alkyl glucoside solution and the mixture was heated to 80° C. The color changed gradually from brown to a light lemon-yellow. The product had a Gardner color at 10 percent concentration of less than 1.

EXAMPLE 8

In a reaction vessel, 50 parts of the 70 percent alkyl glucoside solution were treated with 1 part of a 1:1 sodium perborate:sodium carbonate mixture by the procedure described in Example 7. The resulting product had a Gardner color at a 10 percent concentration in water of less than 1.

EXAMPLE 9

In a reaction vessel, 50 parts of the 70 percent alkyl glucoside solution were treated with 0.5 part of HALOX, a commercially available product which contains 25 percent of dichlorodimethylhydantoin, by warming to 60° C. The color changed from a dark brown to a clear lemon-yellow liquid having a Gardner color at 10 percent concentration in water of less than 1.

EXAMPLE 10

In a reaction vessel, 50 parts of the 70 percent alkyl glucoside solution were warmed with 0.25 part of sodium dichloroisocyanurate (sold by Monsanto as ACL-60). The resulting product had a light yellow color and showed an APHA color value of 30 at a 10 percent concentration in water.

EXAMPLE 11

In a reaction vessel, 50 parts of the 70 percent alkyl glucoside solution were treated with 0.5 part of CHLOROX which is a commercially available sodium hypochlorite solution. The product was a light yellow liquid having a Gardner color of less than 1.

EXAMPLE 12

The procedure of Example 1 was essentially followed except the following ingredients were used:

| | |
|---|---|
| Corn Starch | 414 parts |
| Propylene Glycol | 684 parts |
| ALFOL 1012 | 1,485 parts |
| Sulfuric Acid | 7.2 parts |
| Sodium Hydroxide | 15.6 parts |
| Glycerol | 98 parts |

A 70 percent solution of the resulting purified higher-alkyl glysocide was treated with 7 parts of sodium persulfate.

The properties of the alkyl glycoside were as follows:

| | |
|---|---|
| pH (1% solution) | 8.0 |
| Cloud point (1% solution) | >100° C. |

| -continued | |
|---|---|
| Surface Tension (0.1% solution) | 25.8 dynes/cm |
| Draves Sink Time (0.17% solution) | 23.8 seconds |
| Gardner Color (10% solution) | 3 |

The embodiments of the invention in which an exclusive privilege or property is claimed are defined as followed:

1. A process for purifying crude higher-alkyl glycosides containing residual free higher alcohols, said glycosides obtained by the acid catalyzed reaction of $C_8$–$C_{18}$ aliphatic monohydric alcohols with a source of monosaccharide, which comprises partially distilling a mixture of the crude higher-alkyl glycoside and a hydroxyl containing solvent selected from the group consisting of:

(a) glycerol,
(b) polyoxyalkylene glycols having an average of 3 to about 5 oxyalkylene units selected from oxyethylene and oxypropylene,
(c) $C_1$–$C_4$ alkyl ethers of polyoxyalkylene glycols having about 2 to about 5 oxyalkylene units selected from oxyethylene and oxypropylene, and
(d) $C_1$–$C_4$ alkyl ethers of aliphatic diols, triols, and tetrols having no more than 4 carbon atoms, wherein further, the boiling point of the solvent is at least 10° C. higher than that of the higher alcohol used in the preparation of the higher-alkyl glycoside.

2. The process of claim 1 wherein the amount of the hydroxyl-containing solvent used is from 5 percent to about 20 percent by weight based upon the weight of the higher-alkyl glycoside.

* * * * *